United States Patent
Oral et al.

(10) Patent No.: US 9,827,405 B2
(45) Date of Patent: Nov. 28, 2017

(54) DEVICE AND SYSTEM FOR GASTRIC VOLUME REDUCTION TO FACILITATE WEIGHT LOSS

(75) Inventors: Elif A. Oral, Ann Arbor, MI (US); Hakan Oral, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 675 days.

(21) Appl. No.: 13/700,368

(22) PCT Filed: May 26, 2011

(86) PCT No.: PCT/US2011/038080
§ 371 (c)(1), (2), (4) Date: Jan. 29, 2013

(87) PCT Pub. No.: WO2011/150169
PCT Pub. Date: Dec. 1, 2011

(65) Prior Publication Data
US 2013/0131708 A1    May 23, 2013

Related U.S. Application Data

(60) Provisional application No. 61/348,801, filed on May 27, 2010.

(51) Int. Cl.
*A61F 5/00* (2006.01)
*A61M 29/02* (2006.01)

(52) U.S. Cl.
CPC ........... *A61M 29/02* (2013.01); *A61F 5/0036* (2013.01); *A61F 5/004* (2013.01); *A61F 5/0046* (2013.01)

(58) Field of Classification Search
CPC .................. A61F 5/0003; A61F 5/0013; A61F 5/003–5/0046; A61F 5/0089;
(Continued)

(56) References Cited

U.S. PATENT DOCUMENTS 6,450,946 B1    9/2002    Forsell
6,453,907 B1    9/2002    Forsell
(Continued)

FOREIGN PATENT DOCUMENTS

WO    WO-2006/020929 A2    2/2006
WO    WO-2006/047882 A1    5/2006
WO    WO-2007/113714 A1    10/2007

OTHER PUBLICATIONS

International search resport and written opinion from PCT/US2011/038080 dated Aug. 18, 2011.
(Continued)

*Primary Examiner* — Victor Nguyen
*Assistant Examiner* — Jonathan Hollm
(74) *Attorney, Agent, or Firm* — Marshall, Gerstein & Borun LLP

(57) ABSTRACT

An ingestible gastric volume reduction device (100) is provided that is controllably adjustable between an expanded state and a contracted state. A control subsystem within the device is able to selectively transition the device between both states. Such control can be by way of a biological or chemical sensor (102) in the device, a wireless (RF) receiver (104), or timer. Thus activation of the device whether to expand and fill a gastric volume or to contract to open up the gastric volume may be achieved from internal control (within device) or external control (to the device). The device may be used for patient treatment, by administering the device (e.g., through ingestion) to a gastric region and then controllably increasing and/or decreasing the volume of the device during treatment.

18 Claims, 2 Drawing Sheets

(58) Field of Classification Search
CPC .............. A61F 2005/0016–2005/0023; A61M 25/1018–25/10188; A61M 2025/102–2025/1022
USPC .................................. 606/1, 108, 191–200
See application file for complete search history.

(56) References Cited

U.S. PATENT DOCUMENTS

| | | | |
|---|---|---|---|
| 6,454,699 B1 | 9/2002 | Forsell | |
| 6,460,543 B1 | 10/2002 | Forsell | |
| 6,461,293 B1 | 10/2002 | Forsell | |
| 6,579,301 B1* | 6/2003 | Bales | A61F 5/004 604/96.01 |
| 2004/0186502 A1* | 9/2004 | Sampson | A61F 5/003 606/191 |
| 2006/0058829 A1* | 3/2006 | Sampson | A61F 5/0036 606/192 |
| 2007/0104755 A1 | 5/2007 | Sterling et al. | |
| 2007/0233170 A1 | 10/2007 | Gertner | |
| 2007/0266598 A1 | 11/2007 | Pawlus et al. | |
| 2007/0270930 A1* | 11/2007 | Schenck | A61B 17/12022 623/1.11 |
| 2007/0282387 A1 | 12/2007 | Starkebaum | |
| 2007/0293885 A1 | 12/2007 | Binmoeller | |
| 2008/0147002 A1 | 6/2008 | Gertner | |
| 2008/0161717 A1 | 7/2008 | Gertner | |
| 2008/0167648 A1 | 7/2008 | Gertner | |
| 2008/0188837 A1* | 8/2008 | Belsky et al. | 604/890.1 |
| 2008/0241094 A1 | 10/2008 | Burnett et al. | |
| 2008/0243071 A1* | 10/2008 | Quijano | A61F 5/0003 604/103.02 |
| 2008/0281347 A1 | 11/2008 | Gertner | |
| 2008/0300618 A1 | 12/2008 | Gertner | |
| 2009/0292306 A1* | 11/2009 | Kheradvar et al. | 606/192 |
| 2010/0100116 A1* | 4/2010 | Brister | A61F 5/0036 606/192 |
| 2010/0222642 A1* | 9/2010 | Trovato | 600/37 |
| 2010/0268025 A1* | 10/2010 | Belson | 600/109 |

OTHER PUBLICATIONS

International Preliminary Report on Patentability from Application No. PCT/US11/038080 dated Dec. 6, 2012.

* cited by examiner

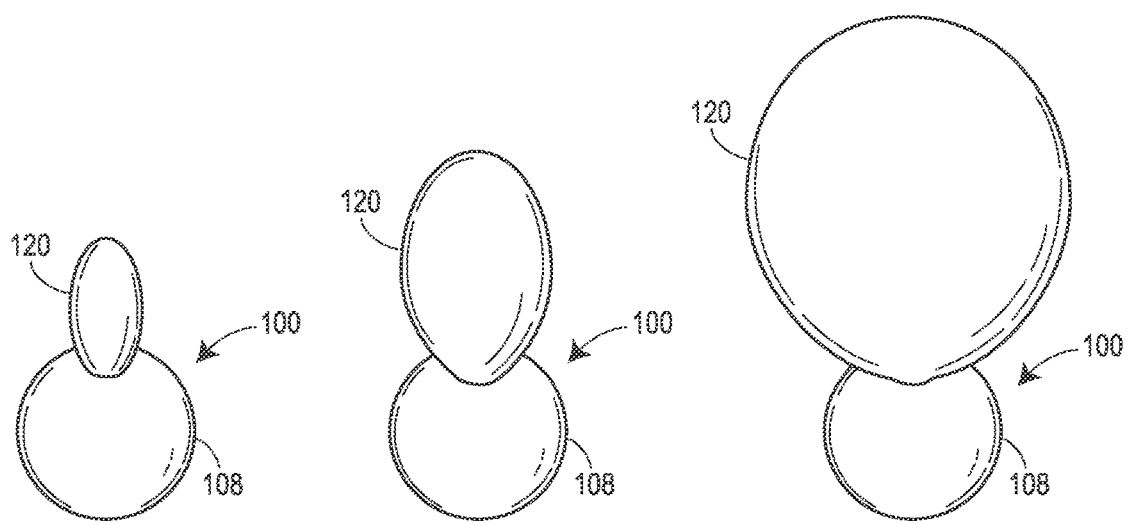
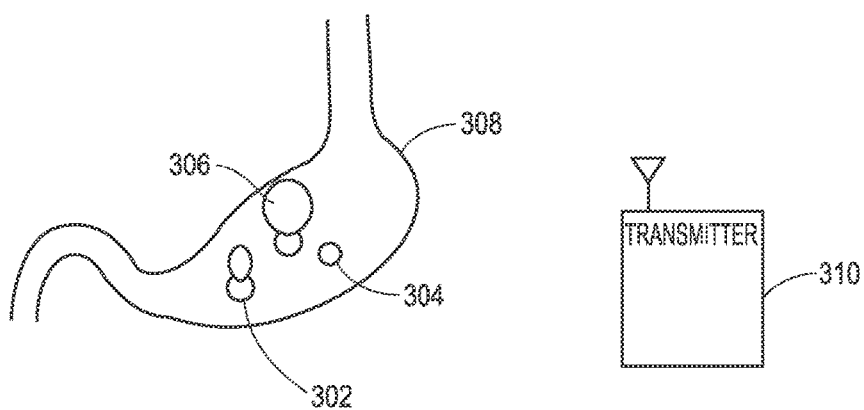

DEVICE AND SYSTEM FOR GASTRIC VOLUME REDUCTION TO FACILITATE WEIGHT LOSS

BACKGROUND OF THE DISCLOSURE

Field of the Disclosure

The disclosure relates generally to techniques for weight loss and, more particularly, to techniques for reducing gastric volume by using a digestible or implantable activator.

Brief Description of Related Technology

Morbid obesity is associated with a significant reduction in survival, and increased risk of co-morbid conditions such as diabetes and heart disease. Often life-style modifications, dietary interventions and exercise may not be sufficient for meaningful weight loss due to a variety of factors such as noncompliance, etc. In recent years bariatric surgery, which involves reduction in gastric volume by using a variety of techniques such as gastric banding, stapling, etc., has evolved as a therapeutic option to promote weight loss. However, the surgery may require significant skill and expertise, and may be associated with considerable risk of complications, morbidity and mortality—most patients with morbid obesity carry a higher surgical risk. Furthermore, recovery may be prolonged; and the procedure is irreversible.

Considering the number of patients with morbid obesity, some researchers have proposed digestible or implantable gastric reduction devices to facilitate weight loss. The techniques have some measure of success, but there are limitations. Intragastric balloons have been proposed reducing gastric volume. Orally administered polymer-based structures that expand in the stomach in response to changes in hydration, pH levels, etc. have also been proposed.

For intragastric balloons, the techniques are invasive and thus less desirable, except in the more extreme cases. In particular, while inflatable balloons can offer internal pumping mechanisms, pressure sensors, and controlled pump release, such features make the devices overly bulky and incapable of either ingestion or passing through the intestines.

For orally administered structures, digestibility requires small devices, which are typically implemented only in a solid-phase change form. This basically means the device is formed of a polymeric outer shell and solid interior that expands in response to environment stimuli contacting that shell. Examples include polymeric formulations such as acid-sensitive, gelatin coatings and dehydration hydrophilic polymers. When ingested the polymeric coating triggers a time release expansion of the device. Unlike implantable balloon devices, the ingestible devices are passable through the pyloric valve in the stomach, but that passing is a result of a solid phase degeneration of the device, and not actively controllable after the device has been ingested into the stomach.

A few orally administrable polymer-based devices that attempt to offer some level of control functionality have been suggested. This includes controlled degradation devices having a plurality of polymer molecules that are each expandable in aqueous solution and releasably coupled through a controlled carrier. The device can selectively release any number of the polymer molecules, each of which then expands based on a solid phase interaction. The technique is limited in a number of ways. For example, polymer release is controlled based on external conditions and not based on conditions measured within the stomach. There is no ability to dynamically control the amount of expansion of each polymer molecule, in particular to controllably reduce the volume of the carrier, for example, to induce device release.

SUMMARY OF THE DISCLOSURE

In an embodiment, an ingestible gastric volume reduction device comprises: a controllably adjustable volume subsystem that in an expansion mode of the device increases the volume of the device and in a contraction mode of the device decreases the volume of the device; and a control subsystem configured to selectively set the mode of the device between the expansion mode and the contraction mode.

In some examples, the device is biologically inert.

In some examples, the control subsystem comprises a sensor.

In some examples, control subsystem comprises a receiver.

In some examples, the control subsystem controls the mode of the device in response to a trigger condition from a sensor or a receiver.

In some examples, the control subsystem is configured to have an activation mode in which the device is activatable for operation after being digested into a gastric cavity.

In some examples, the activation mode is initiated in response to an external signal communicated to the control subsystem from outside the gastric cavity.

In some examples, the control subsystem is configured to set the expansion mode in response to receiving a wireless control signal.

In some examples, the control subsystem is configured to set the expansion mode in response to a sensor within the control subsystem.

In some examples, the volume subsystem includes a titration system capable of releasing a gas agent that expands the volume of the device in response to control from the control subsystem.

In some examples, the titration is capable of releasing another gas agent that reduces the volume of the volume subsystem in response to control from the control subsystem.

BRIEF DESCRIPTION OF THE DRAWING FIGURES

For a more complete understanding of the disclosure, reference should be made to the following detailed description and accompanying drawing figures, in which like reference numerals identify like elements in the figures, and in which:

FIGS. 2A-2C illustrate various stages of expansion/contraction of an ingestible device; and FIG. 3 illustrates an example application of a plurality of ingestible devices each controllable by a wireless transmitter.

Figure 1:
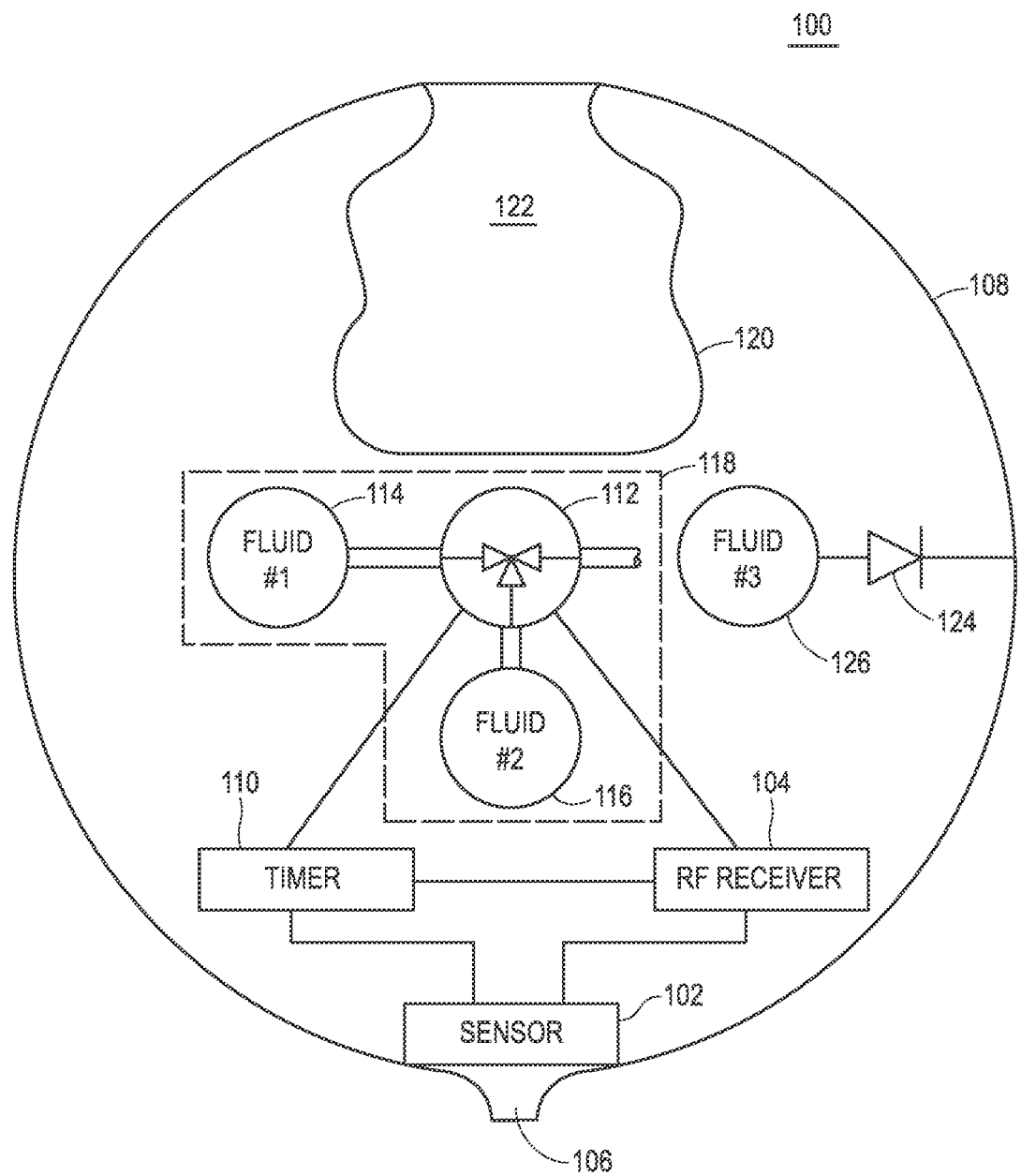
FIG. 1 is an illustration of an ingestible device that is expandable and/or contractible in response to an internal sensor and/or wireless receiver.

While the disclosed methods and apparatus are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF PREFERRED EMBODIMENTS

The present application describes ingestible, biologically inert devices that can be controllably activated after the device has been ingested. The activation may be of a number of different types, but preferably at least three different activation modes may be provided. An initial activation mode is used to set the device for operation. For example, the device may be initially ingested in an inactive state, where the device is unable to expand or contract. The activation mode is then used to turn on the device for operation. Notably, this initiation does not expand or contract the device, but rather activates the device for subsequent expansion or contraction. The next activation mode may be an expansion mode, where the device is controlled to expand in volume to thereby reduce gastric volume of the stomach. As explained further herein, this mode may be achieved through wireless control of a gaseous phase device; while in other examples, this mode may be achieved by sensor devices within the device. Either control mechanism may activate a titration system within the device to release a gas mixture that expands the device. The final mode may be a contraction mode, which reduces the volume of the device using the titration system, for example, by releasing another gas agent that interacts with the gaseous medium to reduce gaseous expansion.

In some examples, the ingestible device may be corrosion resistant and include a radiopaque marker or structure that can be monitored and localized through X-ray fluoroscopy. In some examples, the device may be non-magnetic and thus useful with magnetic resonance imaging, to allow medical personnel to monitor device position and operation after digestion. In some examples, the device may include a transceiver that emits an RF signal to enable an external sensor or sensor array to locate the device within the body.

The ingestible device may include one or multiple inner chambers surrounded by an outer shell, where at least one of the inner chambers contains a pressurized inert gas such as nitrogen, or helium, etc. and an expandable material that may be biodegradable. The ingestible device may include specific biodegradable material that, in an expansion mode, may expand in volume upon contact with water. Example biodegradable materials include hydrogels and/or fluids with a certain pH level.

The device may include various subsystems offering different functionality. One subsystem may be a sensor that responds to an environmental condition, such as for example, a pH sensor, a light sensor, chemical sensor, a muscle contraction sensor, or multiple combinations thereof. These sensors may be initially in an inactive mode when ingested, and then may become activated by a second subsystem in the form of an embedded wireless receiver, or transceiver. By coupling the wireless receiver to the sensor subsystem and the sensor subsystem to a titration subsystem, an integrated system is able to remotely control both expansion and contraction of the ingestible device in a time free manner. "Time free," as used herein, means that the control may be independent from time-based trigger mechanisms, such as those associated with polymer-based solid state activation or those based on an internal timing mechanism, whether electrical, electromechanical, electrochemical, or otherwise.

While time free control is achievable in certain instances, in other instances, the device may operate based on time control, for example, by including an electronic timing circuit within the device. This internal timer may then activate expansion and/or contraction of the device by controlling the release of gases within the device during expansion or control release of a reducing agent during contraction. Upon expansion for example, the timer may be activated once the sensor senses a threshold value of the measured environmental condition. After the sensor has determined the desired condition, the sensor may trigger the timer to start counting until a time period has elapsed and the gaseous phase expands the device. In some examples, the timer which may be executed as a digital or analog counter, and may count the number of times the sensor measures a given environmental condition, such as the number of times or the time period over which a pH sensor has sensed a pH level above a threshold level.

To control expansion and contraction, the ingestible device may include an internal, electrically-controllable valve mechanism capable of gradually releasing gas into the device in response to some initiation. In some examples, the internal timer may control operation of the valve. In other examples, the valve may respond to ingestion of a specific fluid that triggers the valve itself or a sensor coupled thereto, such as a pH sensor. In yet other examples, the wireless receiver may control the valve after receiving a wireless control signal from an external transmitter. The valve mechanism may be continuously adjustable to expand the volume of an internal balloon of the device from between 100 cc to 2000 cc, for example.

The ingestible device may have an expandable balloon or expandable material, having a size is controlled by the valve mechanism of the device. The expandable structure may be biodegradable either substantially, spontaneously upon ingestion of biologically safe fluid that may have certain properties, such as a certain pH, that activate the biodegradation mechanism in the stomach. Or such a biodegrading fluid may be released from an internal reservoir in the device, such as in response to the pH sensor, the internal timer, or the wireless receiver. Alternatively still, the structure may be biodegradable over the course of a period of time, such as 2-8 weeks.

As mentioned above, the device may be reduced in size (e.g., through actively reducing its size or through biodegradation) to pass through the intestinal system through regular peristalsis and expelled from the body. The device may be removed physically, as well, for example through an endoscopic procedure. In some embodiments, the device is extracted using a nasogastric tube or catheter. In some embodiments, the device includes structural members, such as struts, that facilitate grabbing and removing the device.

In some examples the ingestible devices described herein may also release an agent into the stomach along with expansion—these include enzymatic agents, medicinal agents, chemical agents, hormones, or combinations thereof. The release of such agents may be achieved using a check valve in an outer shell of an ingestible device, and coupled to an internal reservoir containing the agent, and controlled by a control mechanism. The control mechanism may include the check valve connected to a fluid reservoir at an inlet, and having an outlet at the outer shell. Under control of a connected timer, sensor, or other processor device (such as an RF receiver), the check valve may be controlled to release the agent stored in the fluid reservoir into the gastric cavity, in response to expansion of the ingestible device.

The applications of the devices discussed herein are numerous and not limited to the particular examples described. The devices may be preferred in patients with obesity in whom initial measures of lifestyle modification, diet and exercise have failed, and prior to consideration of bariatric surgery. In some examples, the techniques herein can be implemented in conjunction with bariatric surgery, particular with patients in whom surgery has failed before or was less than adequate in end result.

Given the variations of design and ease of operation, the devices may be prescribed by internists, gastroenterologists, endocrinologists, and surgeons. The devices may be designed in such a manner than they are programmable by such medical practitioners to control operation of the device. For example, the device may be programmed to stay in the stomach a predetermined period of time, such as between 2-4 weeks, by controlling the timer to release a biodegradation fluid after a predetermined period of time. In fact, a user may program any number of control aspects of the device. The amount of internal balloon expansion may be programmed into the device, the time periods upon which expansion or contraction is to occur may be programmed into the device. Whether the device requires activation after ingestion or is activated prior to ingestion may be programmed into the device. It is contemplated that such programming may be performed through firmware or software updates to the device prior to finally assembling the device with the biologically inert outer shell. However, at least some of these and other programmable features may be set wirelessly through communicating signals to the internal wireless receiver, which would allow for programming of the device after ingestion.

Depending on the gastric size, multiple devices may be used simultaneously within an individual. The devices may be identified in a channelized manner, such that they have been individually communicated with wirelessly, by having each device on a different communication channel. Or multiple devices may be communicated with simultaneously by being assigned to the same communication channel. In any of these examples, known wireless communication techniques may be employed by the external transmitter to effectively communicate with the digested devices.

In comparison to traditional gastric reduction devices based on polymer activation and solid phase change expansion, the present application describes gastric reduction apparatuses that may be realized in a controlled gaseous phase. By using a gaseous phase, devices may be designed, as discussed, to control the timing of gastric expansion. Gas release, for example, may be readily controlled in a time varying manner, whether from static time delay, to control continuous or intermittent time release. Through such control the amount of gastric expansion can be controlled and varied while the gastric reduction device is in the patient. This control includes not only time selective expansion of the volume of the gastric reduction device, but also time selective reduction in the volume of the gastric reduction device. This ability to control both expansion and reduction of an insertable reduction device provides great latitude in patient treatment.

Combining such functionality with wireless activation capabilities adds even further control options. Wireless control may be used to expand the volume of the gastric device and then later reduce volume of that device during the normal operating cycle of the device. By way of example, the device may be activated for expansion on a periodic basis at certain times of the day traditionally associated with meal time. The device may be expanded upon ingestion of food on a regular schedule or upon ingestion of food at a non-scheduled time period. Volume reduction may be performed after the meal has been ingested or after a certain time period after the expansion, for example.

Volume reduction may also occur as a mechanism to induce digestion of the device, so that it is reduced to a size that can pass through the pyloric canal and valve and into the intestines. In this way, a device is provided in which a medical practitioner or individual may actively induce passing of the device without being limited solely to biodegradation for assign the device.

FIG. 1 illustrates an ingestible device 100 in an example implementation. The device includes a sensor 102, which may be any of the sensors described herein, but is described in this example as a pH sensor. An RF receiver 104 is connected to the sensor 102 and is capable of receiving wireless control signals from a wireless transmitter (not shown). The receiver 104 may be a MEMS (microelectromechanical system) device fabricated through MEMS fabrication processes such as photolithography, deposition, and/or etching. The receiver 104 may be compatible with any number of wireless communication protocols, such as any of the IEEE 802.11 standards including IEEE 802.11a, IEEE 802.11b, IEEE 802.11g, and IEEE 802.11n. Other suitable wireless communication protocols include Bluetooth, a short-range communication protocol compared to those of the IEEE 802.11 standards.

The RF receiver 104 may include features as discussed hereinabove, for example, the ability to activate the pH sensor 102 for sensing pH levels of a fluid in the stomach as collected into a sampling region 106 formed via an opening in outer shell 108. Both the RF receiver 104 and the sensor 102 are also coupled to an electronic timer 110 that is used for time-based control as discussed hereinabove. The timer 110 is connected to an electromechanical release valve 112, which in the illustrated example is a three-way valve having two input ports and a release port. The valve 112 may be coupled to a first fluid reservoir 114 to control release of a gaseous agent designed to expand the volume of the device 100. That gaseous agent may be a $CO_2$ or $N_2$ gas held under pressure in the reservoir 114, for example. In other examples, that gaseous agent may be a catalyst that mixes with the ambient environment within the device 100 to produce a gaseous expansion of the volume therein. The valve 112 may also be coupled to a second fluid reservoir 116, which may include a second gaseous agent or other fluid for example a fluid to interact with the gaseous fluid within the device 100 to reduce its over all volume. The second reservoir 116 may include a biodegrading fluid that is released to reduce the size of the device 100 to a size for passing from the stomach through the pyloric canal and valve. In some instances the valve 112 may release fluids from both reservoirs 114, 116 to affect a change in volume of the device. The valve 112 may be controlled wirelessly through a signal communicated to the RF receiver 104, which then controls opening and closing of the valve 112 to release fluid from reservoir 114 and/or reservoir 116.

The valve 112 and fluid reservoirs 114 and 116 form a gaseous titration system 118 within the device and which may be used to controllably expand and contract the volume of the device 100 after the device has been ingested. The RF receiver 104 is one subsystem that is used to control such operation. And the sensor 102 is another subsystem to control such operation. As discussed above, either of these subsystems may permissively control the operation of the other, i.e., activate the other for operation. The sensor 102 may be idle in a non-sensing mode, until the RF receiver 104 receives a turn-on signal from a remote transmitter, after which the RF receiver 104 activates the sensor 102. In another example, the RF receiver 104 is in an idle mode and then only activated to receive wireless control signals after the sensor 102 has sensed a given environmental condition, such as a threshold pH level. In some such examples, the timer 110 may be used to further determine if the sensed level should trigger activation of the RF receiver 104. Of course, the timer 110 may also be used in conjunction with the sensor 102 to determine when to activate the valve 112 in response to environmental conditions alone.

The device 100 includes an expandable, inner balloon 120 that acts to expand in response to the release of gaseous agent from reservoirs 114, 116. The balloon 120 is coupled to the outer shell 108 via a continuous engagement over an opening 122 in the shell 108. By capping this opening, as gas fills the interior of the outer shell 108, the balloon 120 extends through the continuous opening 122 to enlarge the size of the device 100. FIGS. 2A-2C illustrate various expansion stages of the device 100, after an initial amount of expansion is achieved through controlled gas release (FIG. 2A). The device 100 may maintain the device size at this position. Upon application of further gaseous agent, the inner balloon 120 will expand even further (FIG. 2B) until a maximum expansion is achieved (FIG. 2C). The illustrations may be viewed in reverse order to illustrate contraction of the device in response to the sensor 102, the timer 110, or the RF receiver 104.

In some examples, the device 100 may administer an agent to the gastric volume during expansion and/or contraction of the device 100. In some such examples, a check valve 124 may be coupled between an agent fluid reservoir 126 and an outlet on the outer shell 108. The agent may include enzymatic agents, medicinal agents, chemical agents, hormones, or combinations thereof, for example. The check valve 124 may be controlled (connections not shown) by any of the timer 110, the RF receiver 104, the sensor 102, and/or other control mechanisms, as desired.

FIG. 3 illustrates an example use of an ingestible device. A patient has ingested three (3) different ingestible devices 302, 304, and 306 each similar to that of device 100 discussed above. The devices 302, 304, and 306 reside in the patient's stomach 308 and are each controllable to expand or contract therein. A wireless transmitter 310 communicates with these devices 302, 304, and 306 to control such expansion or contraction, or to activate the sensors within each device that control expansion or contraction. The wireless transmitter 310 may be any type of remote communication device, portable or not. Examples include a laptop computer, handheld computer, portable digital assistant (PDA), wireless supported desktop computers, wireless networking devices such as routers, switches, etc. connected to a control computer through a network, or any other computing device.

The wireless transmitter 310 may communicate with each of the devices 302, 304, and 306 in an individualized manner, for example, where each device has been registered as belonging to a different wireless communication channel. In the illustrated example, however, devices 302 and 306 have been assigned to the same wireless channel, such that as the wireless transmitter 310 has communicated with these devices both have been placed into an expansion mode where the devices collectively fill a larger volume of the stomach 308. The device 304 is on another channel and remains in a non-expanded configuration. The ability to control numerous different ingestible devices individually or collectively allows a user to have multiple devices at once to consume a larger volume of the stomach to ensure that as one device degrades another device may be ingested and operated before the degraded device fully degrades and passes through to the intestines. While the devices have been described as part of a multiple channel communication protocol, other protocols may be used, including a single channel, time division multiple access standard, frequency division multiple access standard, or a code division multiple access standard.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. An ingestible and biologically inert gastric volume reduction device comprising:
a controllably adjustable volume subsystem including a titration system being repeatedly adjustable between an expansion mode of the device and a contraction mode of the device, wherein in the expansion mode, the device increases its volume and in the contraction mode, the device decreases its volume, the titration system comprising a first gas agent that expands the volume in the expansion mode and a second gas agent that reacts with the first gas agent to reduce the volume in the contraction mode; and
a control subsystem including a sensor and a receiver coupled to the volume subsystem and configured to repeatedly selectively set the mode of the device between the expansion mode and the contraction mode;
wherein the titration system, in response to control from the control subsystem, is configured to release the first gas agent in the expansion mode and is configured to release the second gas agent in the contraction mode to reduce the volume to a size that is small enough to allow the device to pass through an intestinal system.

2. The device of claim 1, wherein the control subsystem is configured to have an activation mode in which the device is activatable for operation after being digested into a gastric cavity, and wherein the activation mode is initiated in response to an external signal communicated to the control subsystem from outside the gastric cavity.

3. The device of claim 1, wherein the control subsystem is configured to set the expansion mode in response to receiving a wireless control signal at the receiver from a transmitter external to the device.

4. The device of claim 1, wherein the control subsystem is configured to set the expansion mode in response to the sensor in the control subsystem.

5. The device of claim 1, further comprising an expandable outer shell having at least one inner chamber containing an expandable gas, wherein the expandable outer shell is biodegradable.

6. The device of claim 1, wherein the sensor is either a pH sensor, a light sensor, a chemical sensor, a muscle contraction sensor, or a combination thereof.

7. The device of claim 6, wherein the sensor is ingested in an inactive mode, and is configured to be placed into an active mode in response to the control subsystem.

8. The device of claim 1, wherein the control subsystem operates in a time free manner.

9. The device of claim 1, wherein the control subsystem operates in a time controlled manner.

10. The device of claim 1, further comprising an internal discharge subsystem coupled to the control subsystem and to an outlet on an expandable outer shell, wherein the internal discharge subsystem is capable of releasing a third agent into a gastric cavity in response to the device being in the expansion mode or in the contraction mode.

11. The device of claim 10, wherein the third agent is selected from the grouping consisting of enzymatic agents, medicinal agents, chemical agents, hormones and combinations thereof.

12. The device of claim 1, wherein the control subsystem is configured to repeatedly selectively set the mode of the device by controlling the titration system to selectively release at least one of the first gas agent and the second gas agent.

13. The device of claim 1, wherein the titration system comprises a valve coupled to a plurality of reservoirs each adapted to store one of the first gas agent or the second gas agent, the control system adapted to control the release of the first and the second gas agents from the plurality of reservoirs upon selecting the expansion mode or the contraction mode of the device.

14. A system comprising a plurality of the devices of claim 1, wherein each of the plurality of devices is individually controllable to either expand or contract in volume in response to a controller external to each of the plurality of devices.

15. A method of treating a patient comprising:
administering the device of claim 1 to a gastric region of a patient through ingestion by the patient; and
controlling the volume of the device by releasing the first gas agent that expands the volume of the device in the expansion mode and releasing the second gas agent that reduces the volume of the device in the contraction mode to affect an internal volume of the gastric region.

16. The method of claim 15, further comprising controlling the volume of the device using a sensor, a timer, or an RF receiver.

17. The method of claim 15, comprising performing the administering and the controlling in lieu of performing a bariatric procedure on the patient.

18. The method of claim 15, comprising performing the administering and the controlling in combination with a bariatric procedure performed on the patient.

\* \* \* \* \*